United States Patent
Tsukernik (10) Patent No.: US 7,033,376 B2
(45) Date of Patent: *Apr. 25, 2006

(54) INTRAVASCULAR FILTER RETRIEVAL DEVICE AND METHOD

(75) Inventor: Vladimir Tsukernik, West Roxbury, MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 199 days.

This patent is subject to a terminal disclaimer.

(21) Appl. No.: 10/292,143

(22) Filed: Nov. 12, 2002

(65) Prior Publication Data

US 2003/0071285 A1 Apr. 17, 2003

Related U.S. Application Data

(63) Continuation of application No. 09/863,660, filed on May 22, 2001, now Pat. No. 6,558,404, which is a continuation of application No. 09/388,563, filed on Sep. 2, 1999, now Pat. No. 6,251,122.

(51) Int. Cl.
*A61M 29/00* (2006.01)

(52) U.S. Cl. .................................................... 606/200

(58) Field of Classification Search ............... 606/113, 606/114, 127, 159, 200
See application file for complete search history.

(56) References Cited

U.S. PATENT DOCUMENTS

| 3,334,629 A | 8/1967 | Cohn |
| 4,425,908 A | 1/1984 | Simon |
| 4,723,549 A | 2/1988 | Wholey et al. |
| 4,832,055 A | 5/1989 | Palestrant |
| 4,969,891 A | 11/1990 | Gewertz |
| 4,990,156 A | 2/1991 | Lefebvre |
| 5,300,086 A | 4/1994 | Gory et al. |
| 5,324,304 A | 6/1994 | Rasmussen |
| 5,370,657 A | 12/1994 | Irie |
| 5,601,595 A | 2/1997 | Smith |
| 5,626,605 A | 5/1997 | Irie et al. |
| 5,634,942 A | 6/1997 | Chevillon et al. |
| 5,681,347 A | 10/1997 | Cathcart et al. |
| 5,695,504 A | 12/1997 | Gifford, III et al. |
| 5,800,457 A | 9/1998 | Gelbfish |
| 5,810,874 A | 9/1998 | Lefebvre |
| 5,836,969 A | 11/1998 | Kim et al. |
| 5,853,420 A | 12/1998 | Chevillon et al. |
| 6,331,183 B1 * | 12/2001 | Suon ........................ 606/200 |
| 6,391,044 B1 * | 5/2002 | Yadav et al. ............... 606/200 |

* cited by examiner

*Primary Examiner*—Kevin T. Truong
(74) *Attorney, Agent, or Firm*—Crompton, Seager & Tufte LLC (57) ABSTRACT

A thrombus filter configured for placement in within a blood vessel lumen defined by a blood vessel wall. Methods and devices for selectively removing the thrombus filter when the presence of a filter in the vascular system is no longer desired. The thrombus filter includes a first strand formation, a second strand formation, and a joined portion.

4 Claims, 5 Drawing Sheets

FIG. 5

INTRAVASCULAR FILTER RETRIEVAL DEVICE AND METHOD

This application is a continuation of Ser. No. 09/863,660 filed May 22, 2001 now U.S. Pat. No. 6,558,404 which is a continuation of Ser. No. 09/388,563 filed Sep. 2, 1999 now U.S. Pat. No. 6,251,122.

FIELD OF THE INVENTION

The present invention relates generally to filters for use inside blood vessels. More particularly, the present invention relates to thrombus filters which can be securely adjoined at a selected location in the vascular system and selectively removed when the presence of a filter in the vascular system is no longer desired.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

SUMMARY OF THE INVENTION

The present invention pertains to thrombus filters which may be securely adjoined at a selected location in the vascular system and selectively removed when the presence of a filter in the vasculature systems is no longer required. The present invention also pertains to devices and method for removing a thrombus filter using minimally invasive methods. A thrombus filter in accordance with the present invention includes a first strand formation, a second strand formation and a joined portion. The first strand formation and the second strand formation are both comprised of a plurality of strands, each strand having a joined end and a free end. The joined ends of the strands are joined together proximate the joined portion of the thrombus filter. The strands radiate away from the joined portion of the thrombus filter so that the first strand formation and the second strand formation are both generally conical in shape. The strands of the first strand formation and the strands of the second strand formation radiate in generally opposing directions.

When the thrombus filter is disposed in a blood vessel, at least one of the strand formations acts to trap or capture blood clots. The generally conical shape of the strand formation serves to urge captured blood clots toward the center of the blood flow. The flow of blood around the captured blood clots allows the body's natural lysing process to dissolve the clots.

The free ends of the strands act as opposing wall contacting members and serve to position the thrombus filter in the center of a blood vessel lumen. In a presently preferred embodiment, the strands are biased to spring outward. The radial force applied to the walls of the blood vessel by the strand formations assists in preventing migration of the thrombus filter within the blood vessel lumen. The generally opposed orientation of the first strand formation relative to the second strand formation also makes migration of the filter less likely. Migration of the thrombus filter within a blood vessel lumen may also be made less likely by the inclusion of an anchor member proximate the free end of each strand.

In a presently preferred embodiment, a sliding member is disposed about the joined portion of the thrombus filter. One or the other of the strand formations may be collapsed by urging the sliding member toward the free ends of the strands. Urging the sliding member toward the free ends of strands collapses the strand formation from a generally conical shape to a generally cylindrical shape. Once the strand formation is collapsed, it may be urged into the lumen of a retrieval catheter.

With one strand formation in the lumen of the retrieval catheter, the entire thrombus filter may be urged into the lumen of the retrieval catheter. Pulling the thrombus filter in the lumen of the retrieval catheter causes the strands of the second strand formation to collapse from a generally conical shape to a generally cylindrical shape. With all strands in a collapsed position, the thrombus filter may be pulled completely into the lumen of the retrieval catheter. With the thrombus filter disposed inside the lumen of the retrieval catheter, removing the thrombus filter from the body of the patient may be accomplished by withdrawing the retrieval catheter from the blood vessel lumen.

In one embodiment of a retrieval catheter, the retrieval catheter includes an outer tubular member, an inner tubular member and a pulling means. One embodiment of the pulling means includes a plurality of retrieval struts each having a distal end. An engaging member is disposed proximate the distal end of each strut. In one embodiment, each engaging member includes a sharp projection. The distal ends of the struts may be selectively urged inward so that the sharp projections penetrate the sliding member of the thrombus filter. Having thus coupled the struts to the sliding member, a pulling force may be applied to the sliding member by pulling on the proximal ends of the struts.

In an additional embodiment of a retrieval catheter, the pulling means may include flanges fixed to the distal end of each strut. The flanges are adapted to be disposed about the fixed portion of the thrombus filter. In a presently preferred embodiment, the joined portion of the thrombus filter has a generally cylindrical outer surface. Also, in a presently preferred embodiment, each flange includes an inner radius which is substantially equal to the outer radius of the joined portion of the thrombus filter. The flanges may be selectively closed around the joined portion of the thrombus filter. When the flanges are closed around the joined portion of the thrombus filter, they butt against each other to form a generally tubular shell around the joined portion of the thrombus filter.

The strands of one or the other of the strand formations may be urged into a collapsed position by urging the flanges toward the free ends of the strands. The flanges may be urged toward the free ends of the strands by pulling on the proximal ends of the struts. Once the strands have been moved into a collapsed position, the strand formation of the thrombus filter may be positioned within the lumen of a retrieval catheter. This may be accomplished percutaneously by pulling on the proximal end of the struts.

With one of the strand formations positioned within the lumen of the retrieval catheter, the remainder of the thrombus filter may also be urged into the lumen of the retrieval catheter. As described previously, the strands of the second strand formation radiate away from the joined portion of the thrombus filter in a generally opposed direction relative to the strands of the first strand formation. The orientation of the strands allows them to be pulled out of the walls of the blood vessel with minimal force. The strands of the second strand formation may be collapsed by simultaneously pushing on the proximal end of the retrieval catheter and pulling on the proximal ends of the struts.

Pulling the thrombus filter into the lumen of the retrieval catheter causes the strands of the second formation to collapse from a generally conical shape to a generally cylindrical shape. With all of the strands in a collapsed position, the thrombus filter may be pulled completely into the lumen of the retrieval catheter. With the thrombus filter disposed inside the lumen of the retrieval catheter, removing the thrombus filter from the body of the patient may be accomplished by withdrawing the retrieval catheter from the blood vessel lumen.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
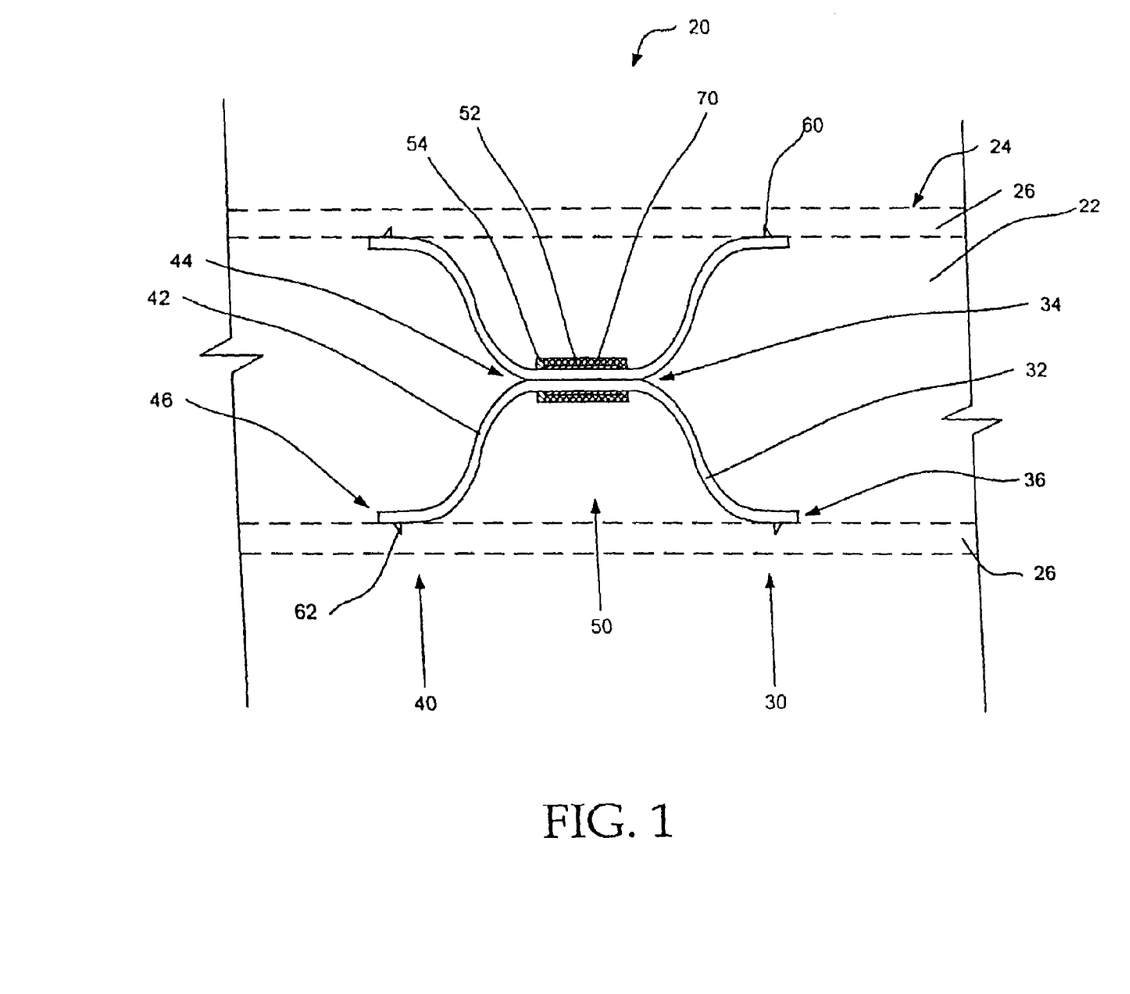
FIG. 1 is a plan view of a thrombus filter positioned in the lumen of a blood vessel lumen.

Reference is now made to the drawings, in which like numbers refer to like elements throughout. FIG. 1 is a plan view of a thrombus filter 20 positioned in a lumen 22 of a blood vessel 24. Blood vessel 24 includes walls 26 which define lumen 22. The main components of thrombus filter 20 are a first strand formation 30, second strand formation 40, and a joined portion 50.

First strand formation 30 and second strand formation 40 are both comprised of a plurality of strands 32 and 42 respectively. Each strand 32 of first strand formation 30 has a joined end 34 and a free end 36. Likewise, each strand 42 of second strand formation 40 has a joined end 44 and a free end 46. Joined ends 34 of strands 32 and joined ends 44 of strands 42 are joined at joined portion 50 of thrombus filter 20.

Strands 32 radiate away from joined portion 50 of thrombus filter 20 so that first strand formation 30 is generally conical in shape. Likewise, strands 42 radiate away from joined portion 50 of the thrombus filter 20 such that second strand formation 40 is generally conical in shape. As shown in FIG. 1, strands 32 of first strand formation 30 and strands 42 of second strand formation 40 radiate in generally opposing directions.

When thrombus filter 20 is disposed in a blood vessel, at least one of the strand formations acts to trap, or capture blood clots. The generally conical shape the strand formation serves to urge captured blood clots toward the center of the blood flow. The flow of blood around the captured blood clots allows the body's natural lysing process to dissolve the clots.

Strands 32 and 42 act as opposing wall contacting members and serve to position thrombus filter 20 in the center of lumen 22 of blood vessel 24. In a presently preferred embodiment, strands 32 and 42 are biased to spring outward. The radial force applied to the walls of the blood vessel by first strand formation 30 and second strand formation 40 assists in preventing migration of thrombus filter 20 within blood vessel lumen 22. The generally opposed orientation of strands 42 relative to strands 32 also makes migration of the filter less likely.

Migration of filter 20 within blood vessel lumen 22 may also made less likely by the inclusion of anchors on thrombus filter 20. An anchor 62 is disposed at free end 46 of each strand 42. Likewise, each free end 36 of each strand 32 includes an anchor 60. In FIG. 1, anchors 60 and 62 are pictured as sharp projections or barbs. It should be understood that anchors 60 and 62 may be comprised of other means for anchoring without departing from the spirit or scope of this invention. It should also be understood that embodiments of thrombus filter 20 which include no anchors are possible without departing from the spirit or scope of the present invention.

Figure 2:
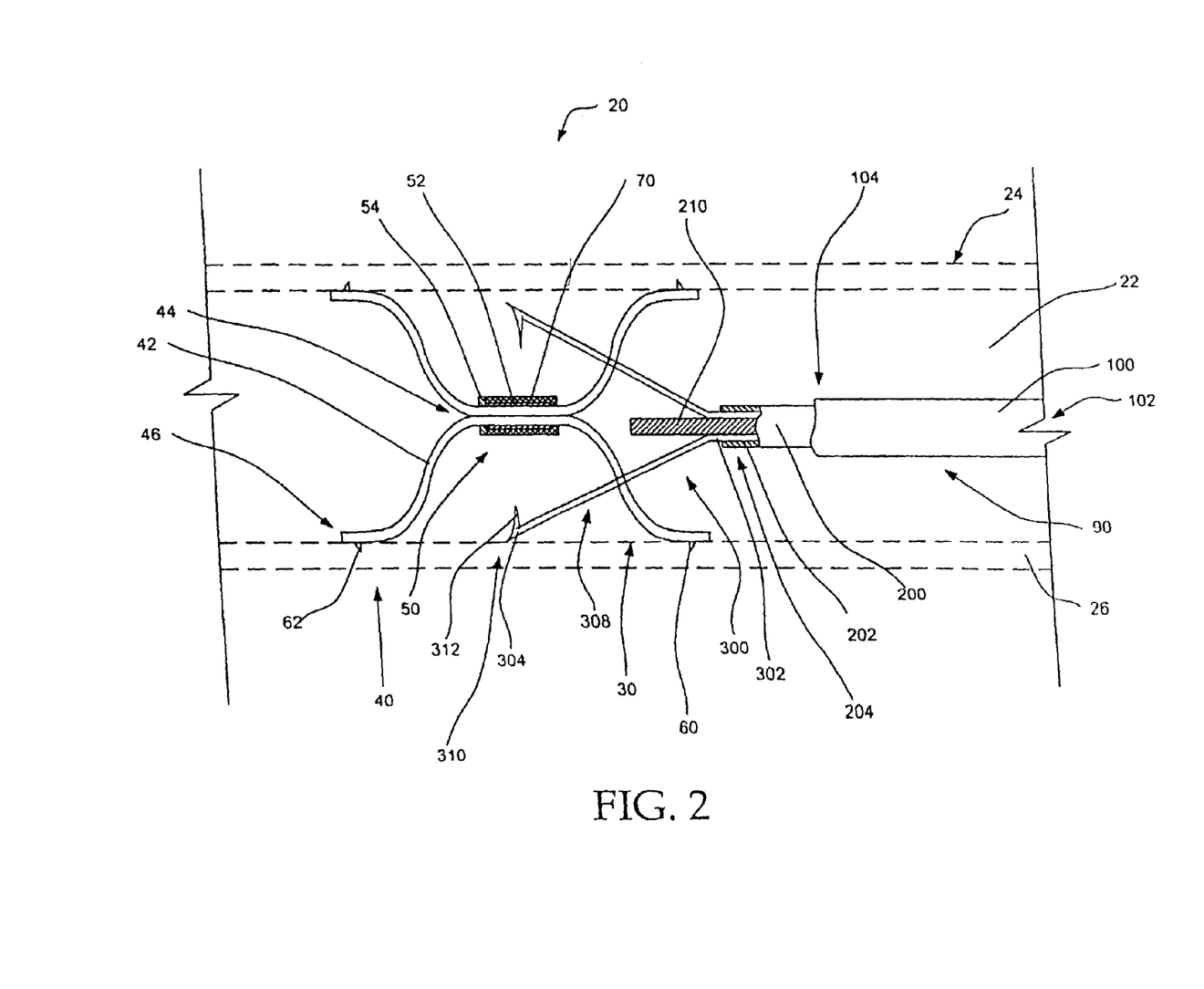
FIG. 2 is a plan view of a removal catheter disposed in a blood vessel lumen proximate the thrombus filter of FIG. 1.

In the embodiment of FIG. 1, joined portion 50 includes a collar 52 disposed about joined ends 34 of strands 32 and joined ends 44 of strands 42. A sliding member 70 is disposed about joined portion 50. In the embodiment of FIG. 2 sliding member 70 is preferably comprised of a plastic material. Examples of suitable plastic materials include polyethylene (PE), polypropylene (PP), thermoset polyurethane, thermoplastic polyurethane, and polyether block amide (PEBA). Those with skill in the art will appreciate that sliding member 70 may be comprised of other materials without deviating from the spirit or scope of the present invention. A ring 54 is fixed to joined portion 50 proximate one end of sliding member 70. Ring 54 may act as a stop to limit the travel of sliding member 70.

Although two strands 32 and two strands 34 are shown in FIG. 1. Any number of strands 32, 34 may be used. In a presently preferred embodiment first strand formation 30 includes between about 3 strands 32 and about 6 strands 32. In a presently preferred embodiment second strand formation 40 includes between about 3 strands 42 and about 6 strands 42.

In a presently preferred embodiment, stands 32, 42 are generally circular in cross section, it should be understood that other cross-sectional shapes are possible without deviating from the spirit or scope of the invention. For example, the cross-sectional shape of stands 32, 42 may be circular, rectangular, square, triangular, oval, etc.

In a presently preferred embodiment, strands 32, 42 are comprised of nickel-titanium alloy. Suitable nickel-titanium alloys are commercially available from Memry Technologies (Brookfield, Conn.), TiNi Alloy Company (San Leandro, Calif.), and Shape Memory Applications (Sunnyvale, Calif.).

Those with skill in the art will appreciate that strands 32, 42 may be comprised of other metallic or non-metallic materials without departing from the spirit or scope of the present invention. Examples of metallic materials which may be suitable for some applications include stainless steel and titanium. Suitable, non-metallic materials may be selected from the following list, which is not exhaustive: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

FIG. 2 is a plan view of a removal catheter 90 disposed in blood vessel lumen 22 proximate thrombus filter 20. Removal catheter 90 includes an outer tubular member 100 having a lumen 102, a distal end 104, and a proximal end 106 (not shown).

In the embodiment of FIG. 2, an inner tubular member 200 is disposed within lumen 102 of outer tubular member 100. Inner tubular member 200 includes a lumen 202, a distal end 204, and a proximal end 206 (not shown). An elongate shaft 210 and a pulling means 300 are disposed within lumen 202 of inner tubular member 200.

Pulling means 300 includes a plurality of retrieval struts 302 each having a distal end 304, a proximal end 306 (not shown), and a distal portion 308. An engaging member 310 is disposed proximate the distal end 304 of each strut 302. In the embodiment of FIG. 2, each engaging member 310 includes a sharp projection 312.

In the embodiment of FIG. 2, distal portions 308 of retrieval struts 302 are biased to spring outward. Distal portions 308 of retrieval struts 302 may be selectively urged inward by urging distal end 204 of inner tubular member 200 toward distal ends 304 of retrieval struts 302. During, a surgical procedure, this may be accomplished percutaneously by pushing on proximal end 206 (not shown) of inner tubular member 200, and/or pulling on proximal ends 306 (not shown) of retrieval struts 302.

A method of removing thrombus filter 20 from blood vessel lumen 22 may now be described with reference to FIG. 2. The retrieval process typically begins by introducing catheter 90 into the patients vascular system. The retrieval catheter typically enters the patients vascular system at a point which is readily accessible to the physician. Once in the vascular system, the retrieval catheter is urged forward until distal end 104 of outer tubular member 100 is proximate thrombus filter 20.

For example, if thrombus filter 20 is located in the inferior vena cava of a patient's vascular system, removal catheter 90 may enter the vascular system at the femoral vein. Alternately, if thrombus filter 20 is located in the superior vena cava of a patient's vascular system, removal catheter 90 may enter the vascular system at the jugular vein. In either case, the filter removal procedure is minimally invasive, and generally does not require general anesthesia.

Preferably, distal portions 308 of retrieval struts 302 will be in a retracted position while the distal end of retrieval catheter 90 is advanced through the vasculature. Distal portions 308 may be held in a retracted position by inner tubular member 200. When the distal end of catheter 90 is proximate thrombus filter 20 inner tubular member 200 may be pulled back, allowing distal portions 308 of struts 302 to spring outward. Struts 302 may then be urged forward until distal ends 304 of struts 302 are proximate slide 70 of thrombus filter 20.

Distal portions 308 of struts 302 may then be urged towards slide 70 by urging distal end 204 of inner tubular member 200 toward distal ends 304 of struts 302. This may be accomplished percutaneously by simultaneously pushing on distal end 206 of inner tubular member 200 and pulling on distal ends 306 of struts 302. When distal portions 308 of struts 302 are closed onto slide 70, sharp projections 312 penetrate into slide 70.

A pulling force may then be applied to slide 70. In a presently preferred embodiment, this pulling force is created by pulling on proximal ends 306 of struts 302. Also in a presently preferred embodiment, thrombus filter 20 may be held in position by pushing the distal end of elongate shaft 210 against thrombus filter 20.

Strands 32 may be urged into a collapsed position by urging slide 70 toward free ends 36 of strands 32. Once strands 32 have been moved to a collapsed position, first strand portion 30 of thrombus filter 20 may be positioned within lumen 102 of outer tubular member 100. This may be accomplished percutaneously by pushing on proximal end 106 of outer tubular member 100 and/or pulling on proximal ends 306 of struts 302.

Once first strand formation 30 is positioned within lumen 102 of outer tubular member 100, the remainder of thrombus filter 20 may also be urged into lumen 102 of outer tubular member 100. As described previously, strands 42 of second strand formation 40 radiate away from joined portion 50 of thrombus filter 20 in a generally opposed direction relative to strands 32 of first strand formation 30. The orientation of strands 42 allows them to be pulled out of walls 26 of blood vessel 22 with minimal force. Strands 42 may be converted to a collapsed position by simultaneously by pushing on proximal end 106 of outer tubular member 100 and pulling on proximal ends 306 of struts 302.

Pulling thrombus filter 20 into lumen 102 of outer tubular member 100 causes strands 42 to collapse causing second strand formation 40 to transform from a generally conical shape to a generally cylindrical shape. With strands 32 and strands 42 in a collapsed position, thrombus filter 20 may be pulled completely into lumen 102 of outer tubular member 100. With thrombus filter 20 disposed inside lumen 102 of outer tubular member 100, removing thrombus filter 20 from the body of the patient may be accomplished by withdrawing retrieval catheter 90 from blood vessel lumen 22.

Figure 3:
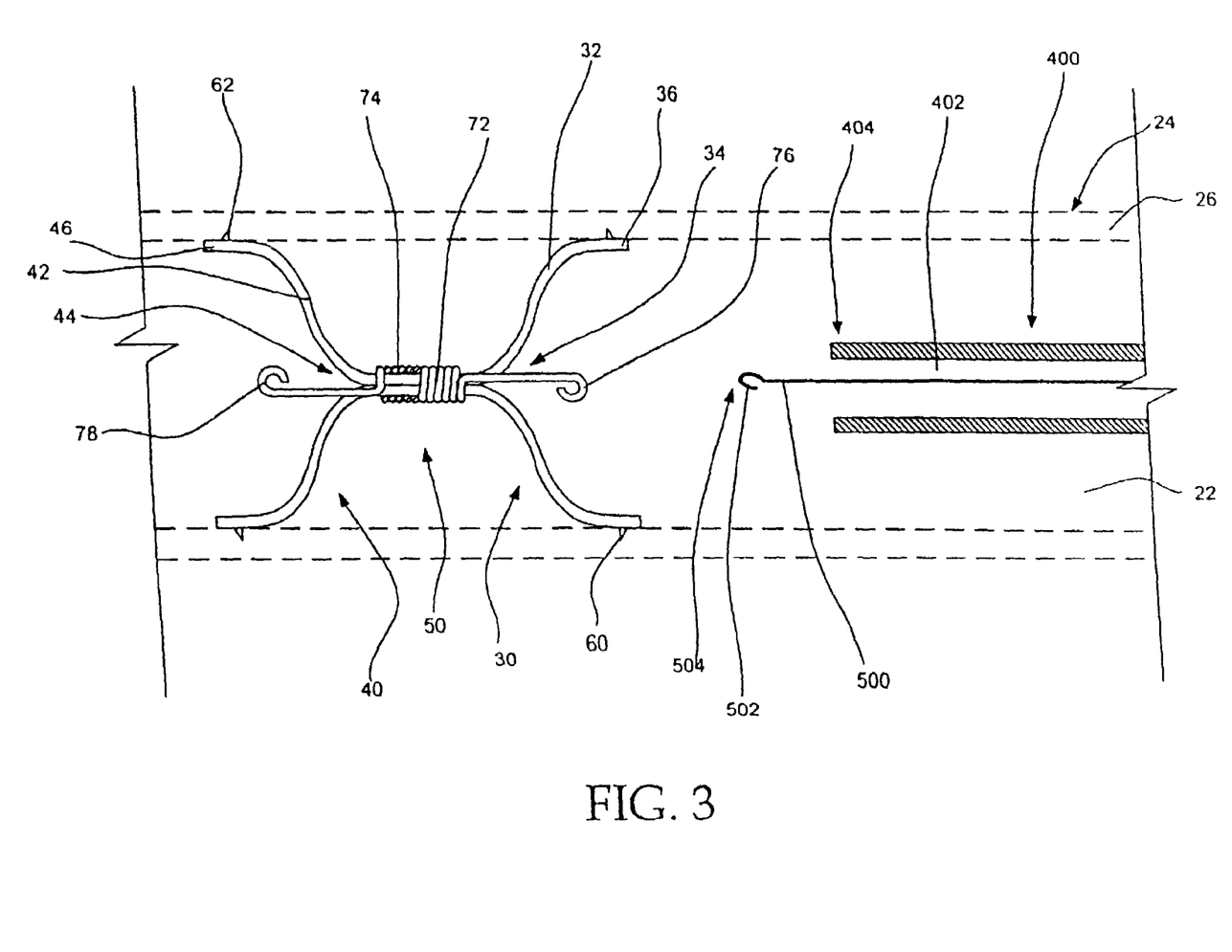
FIG. 3 is a plan view of an alternate embodiment of a thrombus filter and a removal catheter positioned in the lumen of a blood vessel lumen.

FIG. 3 is a plan view of an alternate embodiment of thrombus filter 20 positioned in a lumen 22 of a blood vessel 24. Blood vessel 24 includes walls 26 which define lumen 22. The main components of thrombus filter 20 are a first strand formation 30, second strand formation 40, and a joined portion 50.

First strand formation 30 and second strand formation 40 are both comprised of a plurality of strands 32 and 42 respectively. Each strand 32 of first strand formation 30 has a joined end 34 and a free end 36. Likewise, each strand 42 of second strand formation 40 has a joined end 44 and a free end 46. Joined ends 34 of strands 32 and joined ends 44 of strands 42 are joined at joined portion 50 of thrombus filter 20. In the embodiment of FIG. 3, joined portion 50 includes solder 56. Solder 56 is used to fix joined ends 34 of strands 32 and joined ends 44 of strands 42 together. Other methods may be used to fix joined ends 34, 44 of strands 32, 42 without departing from the spirit or scope of the present invention. For example, brazing, welding, mechanical fasteners, and the use of adhesives may be suitable for some applications.

Strands 32 radiate away from joined portion 50 of thrombus filter 20 so that first strand formation 30 is generally conical in shape. Likewise, strands 42 radiate away from joined portion 50 of the thrombus filter 20 such that second strand formation 40 is generally conical in shape. As shown in FIG. 1, strands 32 of first strand formation 30 and strands 42 of second strand formation 40 radiate in generally opposing directions.

When thrombus filter 20 is disposed in a blood vessel, at least one of the strand formations acts to trap, or capture blood clots. The generally conical shape the strand formation serves to urge captured blood clots toward the center of the blood flow. The flow of blood around the captured blood clots allows the body's natural lysing process to dissolve the clots.

Strands 32 and 42 act as opposing wall contacting members and serve to position thrombus filter 20 in the center of lumen 22 of blood vessel 24. In a presently preferred embodiment, strands 32 and 42 are biased to spring outward. The radial force applied to the walls of the blood vessel by first strand formation 30 and second strand formation 40 assists in preventing migration of thrombus filter 20 within blood vessel lumen 22. The generally opposed orientation of strands 42 relative to strands 32 also makes migration of the filter less likely.

Migration of filter 20 within blood vessel lumen 22 may also made less likely by the inclusion of anchors on thrombus filter 20. An anchor 62 is disposed at free end 46 of each strand 42. Likewise, each free end 36 of each strand 32 includes an anchor 60. In FIG. 1, anchors 60 and 62 are pictured as sharp projections or barbs. It should be understood that anchors 60 and 62 may be comprised of other means for anchoring without departing from the spirit or scope of this invention. It should also be understood that embodiments of thrombus filter 20 which include no anchors are possible without departing from the spirit or scope of the present invention.

Two slides 72 and 74 are disposed about joined portion 50. In the embodiment of FIG. 3 each sliding member 70, 74 is comprised of a helical coil. The strength of slides 72, 74 may be increased by soldering or otherwise bonding consecutive turns of the helical coil to each other. In FIG. 3, slide 74 is shown in partial cross section. Slides 72, 74 include coupling members 76, 78 respectively.

In FIG. 3, a removal catheter 400 is disposed in lumen 22 of blood vessel 24. Removal catheter 400 includes a lumen 402, a distal end 404, and a proximal end 406 (not shown). An elongate member 500 is disposed in lumen 402 of removal catheter 400. Elongate member 500 includes a distal end 504, a proximal end 506 (not shown), and a coupling member 502 disposed proximate distal end 504.

A method of removing thrombus filter 20 from blood vessel lumen 22 may now be described with reference to FIG. 3. The retrieval process typically begins by introducing the catheter into the patients vascular system. The retrieval catheter typically enters the patients vascular system at a point which is readily accessible to the physician. Once in the vascular system, the retrieval catheter is urged forward until distal end 404 is proximate thrombus filter 20.

For example, if thrombus filter 20 is located in the inferior vena cava of a patient's vascular system, removal catheter 400 may enter the vascular system at the femoral vein. Alternately, if thrombus filter 20 is located in the superior vena cava of a patient's vascular system, removal catheter 400 may enter the vascular system at the jugular vein. In either case, the filter removal procedure is minimally invasive, and generally does not require general anesthesia.

The retrieval catheter is advanced through blood vessel lumen 22 until distal end 404 catheter 400 is proximate thrombus filter 20. Distal end 504 of elongate member 500 is then coupled to sliding member 72. This may be accomplished by mating coupling member 502 of elongate member 500 with coupling member 76 of the sliding member 72. A pulling force is then applied to sliding member 72. In a presently preferred embodiment, this pulling force is created by pulling on proximal end 506 (not shown) of elongate member 500.

Pulling on sliding member 72 urges sliding member 72 toward free ends 36 of strands 32. As sliding member 72 moves, it causes strands 32 to collapse. Once strands 32 move to a collapsed position, first strand formation 30 of thrombus filter 20 may be urged into lumen 402 of retrieval catheter 400.

Once first strand formation 30 has entered lumen 402 of retrieval catheter 400, thrombus filter 20 may be urged further into lumen 402 of catheter 400. As described previously, strands 42 of second strand formation 40 radiate away from joined portion 50 of thrombus filter 20 in a generally opposed direction relative to strands 32 of first strand formation 30. The orientation of strands 42 allows them to be pulled away from walls 26 of blood vessel 24 with minimal force.

Pulling thrombus filter 20 into lumen 402 of retrieval catheter 400 causes strands 42 to collapse causing second strand formation 40 to transform from a generally conical shape to a generally cylindrical shape. The collapse of strands 32 and 42 allows all of thrombus filter 20 to be disposed in lumen 402 of catheter 400. With thrombus filter 20 disposed inside lumen 402 of retrieval catheter 400, removing thrombus filter 20 from the body of the patient may be accomplished by withdrawing retrieval catheter 400 from blood vessel lumen 22.

An additional method of removing thrombus filter 20 from blood vessel lumen 22 has been envisioned in which two removal catheters 400A and 400B are utilized. This method may be described with reference to FIG. 4.

Figure 4:
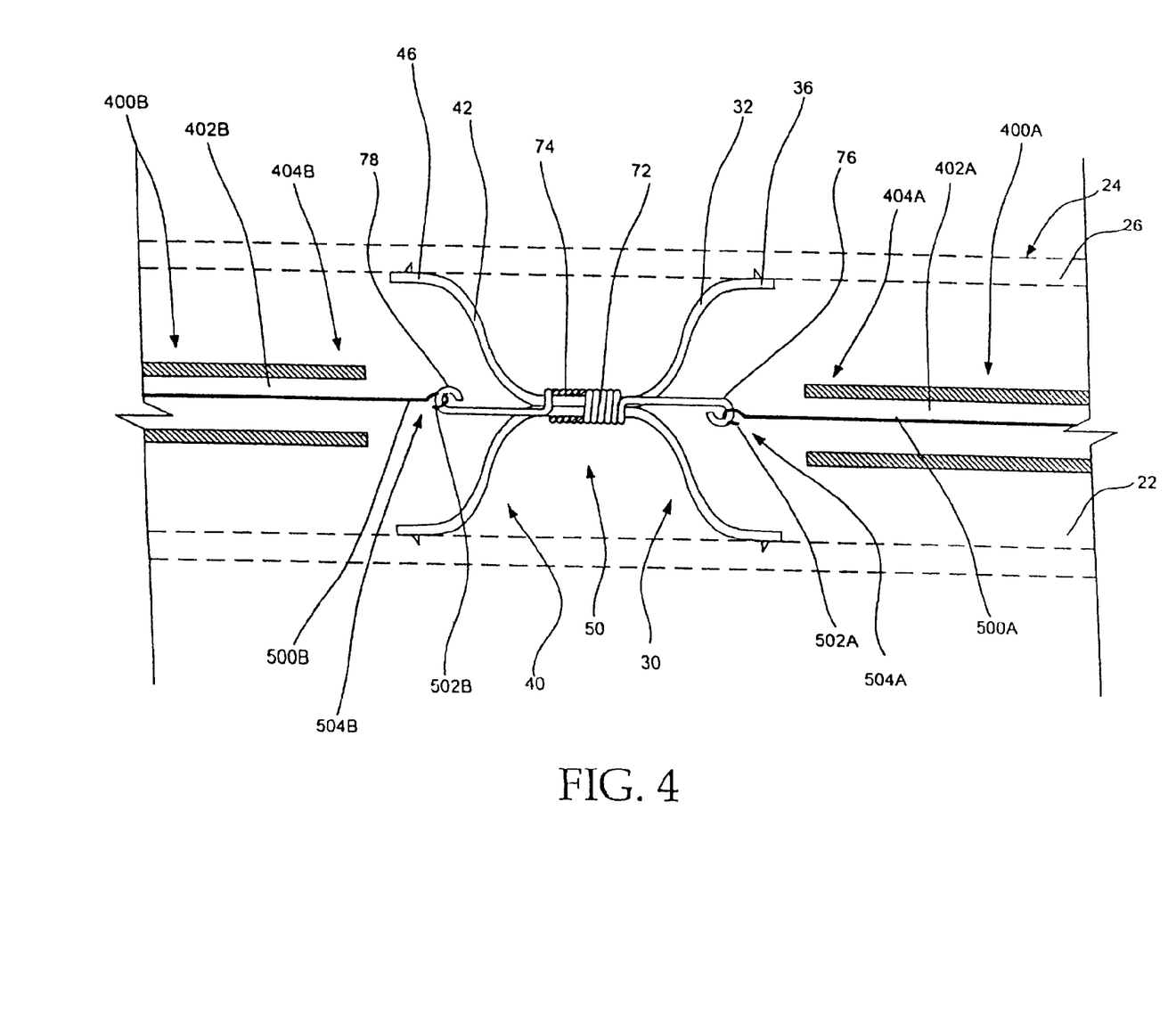
FIG. 4 is a plan view of the thrombus filter of FIG. 3 illustrating an alternate method of removal.

The retrieval process typically begins by introducing catheters 400A, 400B into the patients vascular system. Once in the vascular system, retrieval catheters 400A, 400B are urged forward until distal ends 404A, 404B are proximate thrombus filter 20.

Retrieval catheters 400A, 400B enter the patient's vascular system at points which allow them to approach thrombus filter 20 from substantially opposing directions. For example, removal catheter 400A may enter the vascular system at the femoral vein and removal catheter 400B may enter the vascular system at the patients right internal jugular vein.

Retrieval catheter 400A is advanced through the vasculature of the patient until distal end 404A of catheter 400A is proximate first strand formation 30 of thrombus filter 20. Likewise, retrieval catheter 400B is advanced through the vasculature of the patient until distal end 404A of catheter 400B is proximate second strand formation 40 of thrombus filter 20

Distal end 504A of elongate member 500A is then coupled to sliding member 72. This may be accomplished by mating coupling member 502A of elongate member 500A with coupling member 76 of the sliding member 72. Likewise, distal end 504B of elongate member 500B is coupled to sliding member 74. This may be accomplished by mating coupling member 502B of elongate member 500B with coupling member 78 of the sliding member 74.

Sliding member 72 may now be urged towards distal ends 36 of strands 32 by applying a pulling force to proximal end 506A (not shown) of elongate member 500A. Simultaneously, sliding member 74 may now be urged towards distal ends 46 of strands 42 by applying a pulling force to proximal end 506B (not shown) of elongate member 500B.

Urging sliding member 72 toward free ends 36 of strands 32 causes first strand formation 30 to collapse. Likewise, urging sliding member 74 toward free ends 46 of strands 42 causes second strand formation 40 to collapse.

Once strands 32, 42 move to a collapsed position, thrombus filter 20 may be urged into lumen 402A of retrieval catheter 400A. Alternately, thrombus filter 20 may be pulled into lumen 402B of retrieval catheter 400B. With thrombus filter 20 disposed inside the lumen of a of retrieval catheter, removing thrombus filter 20 from the body of the patient may be accomplished by withdrawing the retrieval catheter from blood vessel lumen 22.

Other embodiments have been envisioned. For example, sliding member 72 and sliding member 74 may be replaced with one sliding member comprised of a continuous helical coil. In this embodiment, pulling in opposing directions on coupling members 76, 78 would cause the helical coil to expand in length.

Figure 5:
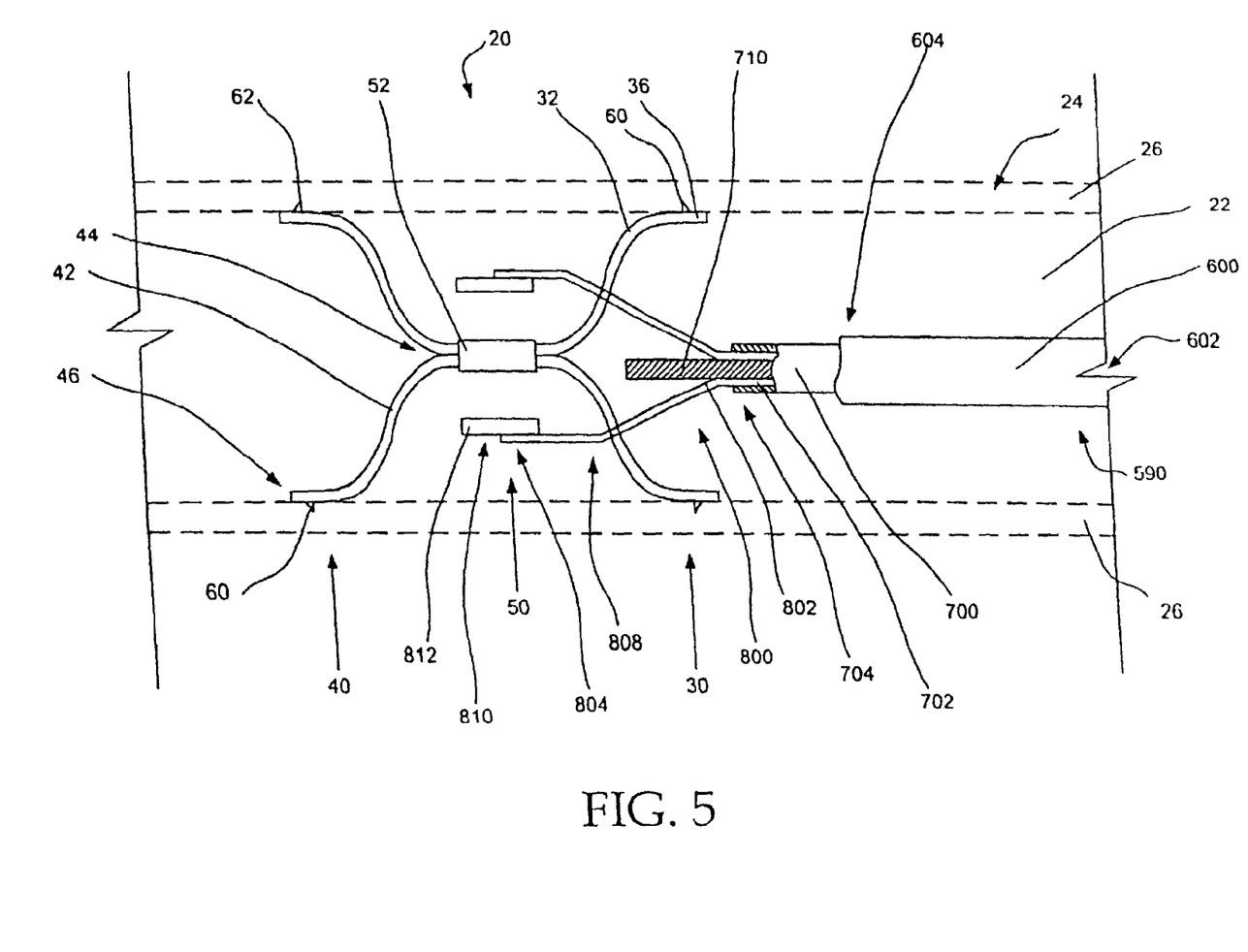
FIG. 5 is a plan view of an alternate embodiment of a thrombus filter and removal catheter.

FIG. 5 is a plan view of an alternate embodiment of thrombus filter 20 positioned in a lumen 22 of a blood vessel 24. Blood vessel 24 includes walls 26 which define lumen 22. The main components of thrombus filter 20 are a first strand formation 30, second strand formation 40, and a joined portion 50.

First strand formation 30 and second strand formation 40 are both comprised of a plurality of strands 32 and 42 respectively. Each strand 32 of first strand formation 30 has a joined end 34 and a free end 36. Likewise, each strand 42 of second strand formation 40 has a joined end 44 and a free end 46. Joined ends 34 of strands 32 and joined ends 44 of strands 42 are joined at joined portion 50 of thrombus filter 20. In the embodiment of FIG. 5, joined portion 50 includes a collar 52 disposed about joined ends 34, 44 of strands 32, 42.

Strands 32 radiate away from joined portion 50 of thrombus filter 20 so that first strand formation 30 is generally conical in shape. Likewise, strands 42 radiate away from joined portion 50 of the thrombus filter 20 such that second strand formation 40 is generally conical in shape. As shown in FIG. 5, strands 32 of first strand formation 30 and strands 42 of second strand formation 40 radiate in generally opposing directions.

When thrombus filter 20 is disposed in blood vessel lumen 22, at least one of the strand formations acts to trap, or capture blood clots. The generally conical shape the strand formation serves to urge captured blood clots toward the center of the blood flow. The flow of blood around the captured blood clots allows the body's natural lysing process to dissolve the clots.

Strands 32 and 42 act as opposing wall contacting members and serve to position thrombus filter 20 in the center of lumen 22 of blood vessel 24. In a presently preferred embodiment, strands 32 and 42 are biased to spring outward. The radial force applied to the walls of the blood vessel by first strand formation 30 and second strand formation 40 assists in preventing migration of thrombus filter 20 within blood vessel lumen 22. The generally opposed orientation of strands 42 relative to strands 32 also makes migration of the filter less likely.

Migration of filter 20 within blood vessel lumen 22 may also made less likely by the inclusion of anchors on thrombus filter 20. An anchor 62 is disposed at free end 46 of each strand 42. Likewise, each free end 36 of each strand 32 includes an anchor 60. In FIG. 5, anchors 60 and 62 are pictured as sharp projections or barbs. It should be understood that anchors 60 and 62 may be comprised of other means for anchoring without departing from the spirit or scope of this invention. It should also be understood that embodiments of thrombus filter 20 which include no anchors are possible without departing from the spirit or scope of the present invention.

FIG. 5 includes a removal catheter 590 disposed in blood vessel lumen 22 proximate thrombus filter 20. Removal catheter 590 includes an outer tubular member 600 having a lumen 602, a distal end 604, and a proximal end 606 (not shown).

In the embodiment of FIG. 5, an inner tubular member 700 is disposed within lumen 602 of outer tubular member 600. Inner tubular member 700 includes a lumen 702, a distal end 704, and a proximal end 706 (not shown). An elongate shaft 710 and a pulling means 800 are disposed within lumen 702 of inner tubular member 700.

Pulling means 800 includes a plurality of struts 802 each having a distal end 804, a proximal end 806 (not shown), and a distal portion 808. An engaging member 810 is disposed proximate the distal end 804 of each strut 802. In the embodiment of FIG. 5, each engaging member 810 includes a flange 812. Flanges 812 are adapted to be disposed about collar 52 of thrombus filter 20. In a presently preferred embodiment, collar 52 has a generally cylindrical outer surface. Also in a presently preferred embodiment each flange 812 includes an inner radius which is substantially equal to the outer radius of collar 52. When flanges 812 are closed around collar 52 they butt against each other to form a generally tubular shell around collar 52.

In the embodiment of FIG. 5, distal portions 808 of retrieval struts 802 are biased to spring outward. Distal portions 808 of retrieval struts 802 may be selectively urged inward by urging distal end 704 of inner tubular member 700 toward distal ends 804 of retrieval struts 802. During a surgical procedure, this may be accomplished percutaneously by pushing on proximal end 706 (not shown) of inner tubular member 700, and/or pulling on proximal ends 806 (not shown) of retrieval struts 802.

A method of removing thrombus filter 20 from blood vessel lumen 22 may now be described with reference to FIG. 5. The retrieval process typically begins by introducing catheter 590 into the patients vascular system. Once in the vascular system, the retrieval catheter is urged forward until distal end 604 of outer tubular member 600 is proximate thrombus filter 20.

Preferably, distal portions 808 of retrieval struts 802 will be in a retracted position while the distal end of retrieval catheter 590 is advanced through the vasculature. Distal portions 808 may be held in a retracted position by inner tubular member 700.

When the distal end of catheter 590 is proximate thrombus filter 20 inner tubular member 700 may be pulled back, allowing distal portions 808 of struts 802 to spring outward. Struts 802 may then be urged forward until distal ends 804 of struts 802 are proximate joined portion 50 of thrombus filter 20.

Distal portions 808 of struts 802 may then be urged towards joined portion 50 by urging distal end 604 of inner tubular member 700 toward distal ends 804 of struts 802. This may be accomplished percutaneously by simultaneously pushing on distal end 706 (not shown) of inner tubular member 700 and pulling on distal ends 806 of struts 802. When distal portions 808 of struts 802 are closed onto joined portion 50, flanges 812 close around collar 52. Flanges 812 are adapted so that they butt together and form a substantially tubular shell around collar 52.

Strands 32 may be urged into a collapsed position by urging flanges 812 toward free ends 36 of strands 32. Flanges 812 may be urged toward free ends 36 of strands 32 by pulling on proximal ends 806 of struts 802. In a presently preferred method, thrombus filter 20 may be held in position by pushing the distal end of elongate shaft 710 against thrombus filter 20. Once strands 32 have been moved to a collapsed position, first strand portion 30 of thrombus filter 20 may be positioned within lumen 602 of outer tubular member 600. This may be accomplished percutaneously by pushing on proximal end 606 of outer tubular member 600 and/or pulling on proximal ends 806 of struts 802.

Once first strand formation 30 is positioned within lumen 602 of outer tubular member 600, the remainder of thrombus filter 20 may also be urged into lumen 602 of outer tubular member 600. As described previously, strands 42 of second strand formation 40 radiate away from joined portion 50 of thrombus filter 20 in a generally opposed direction relative to strands 32 of first strand formation 30. The orientation of strands 42 allows them to be pulled out of walls 26 of blood vessel 22 with minimal force. Strands 42 may be converted to a collapsed position by simultaneously by pushing on proximal end 606 of outer tubular member 600 and pulling on proximal ends 806 of struts 802.

Pulling thrombus filter 20 into lumen 602 of outer tubular member 600 causes strands 42 to collapse causing second strand formation 40 to transform from a generally conical shape to a generally cylindrical shape. With strands 32 and strands 42 in a collapsed position, thrombus filter 20 may be pulled completely into lumen 602 of outer tubular member 600. With thrombus filter 20 disposed inside lumen 602 of outer tubular member 600, removing thrombus filter 20 from the body of the patient may be accomplished by withdrawing retrieval catheter 590 from blood vessel lumen 22.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A thrombus filter element for placement within a blood vessel lumen defined by a blood vessel wall comprising:
   a filter having a filtering portion, the filter having a first position and a second position;
   a sliding member;
   wherein when the sliding member is in a first location, the filter is in the first position and when the sliding member is in a second location, the filter is in the second position, wherein the sliding member is slidably disposed on the filtering portion in at least one of the first and second positions.

2. The thrombus filter element of claim 1 wherein, when the filter is in the first position, the filter may not be moved with respect to the blood vessel wall.

3. The thrombus filter element of claim 1 wherein, when the filter is in the second position, the filter may be moved with respect to the blood vessel wall.

4. A thrombus filter element for placement within a blood vessel lumen defined by a blood vessel wall comprising:
   a filter having a filtering portion, the filter having a first position and a second position; and
   a sliding member having a lumen therethrough,
   wherein the filter is at least partially disposed in the lumen of the sliding member,
   wherein the filtering portion comprises struts that splay outward when in an unconstrained position,
   wherein when the sliding member is in a first location, the filter is in the first position and when the sliding member is in a second location, the filter is in the second position, wherein the sliding member is slidably disposed on the filtering portion in at least one of the first and second positions.

* * * * *